United States Patent [19]

Chin

[11] 4,400,529
[45] Aug. 23, 1983

[54] HERBICIDE ANTIDOTE COMPOSITIONS AND METHOD OF USE

[75] Inventor: Hsiao-Ling M. Chin, Walnut Creek, Calif.

[73] Assignee: Stauffer Chemical Company, Westport, Conn.

[21] Appl. No.: 360,292

[22] Filed: Mar. 22, 1982

[51] Int. Cl.³ .......................................... C07C 149/43
[52] U.S. Cl. ........................................ 560/16; 560/34; 560/47; 560/168; 560/169; 71/106; 71/107; 71/111; 71/120
[58] Field of Search ..................... 560/16, 34, 47, 168, 560/169; 71/106, 107, 111, 120

[56] References Cited

U.S. PATENT DOCUMENTS

| | | | |
|---|---|---|---|
| 3,879,190 | 4/1975 | Fuchs | 560/168 |
| 3,954,837 | 5/1976 | Belliner | 560/16 |
| 3,959,331 | 5/1976 | Fuchs | 560/16 |
| 4,014,924 | 3/1977 | Fuchs | 560/16 |

*Primary Examiner*—Paul J. Killos
*Attorney, Agent, or Firm*—Paul R. Martin

[57] ABSTRACT

Herbicide antidote compounds, compositions, and methods of use are disclosed in which compounds of the formula

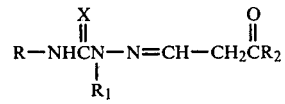

wherein R can be selected from the group consisting of alkyl groups having from about 1 to about 7 carbon atoms, aryl, and substituted aryl groups in which the substituent group can be lower alkyl having from about 1 to about 3 carbon atoms, substituted lower alkyls of from about 1 to about 3 carbon atoms in which the substituent group is halogen or nitro, lower alkoxy having from about 1 to about 3 carbon atoms; $R_1$ can be selected from the group consisting of hydrogen or lower alkyl having from about 1 to about 6 carbon atoms; $R_2$ can be selected from the group consisting of lower alkoxy having from about 1 to about 3 carbon atoms, and X is oxygen or sulfur; are disclosed as suitable for use as suitable for use as herbicide antidotes, when used in conjunction with thiolcarbamate herbicides. Methods of use include applying the antidote compounds to the soil or to the crop seeds either by themselves or in combination with thiolcarbamate herbicides.

19 Claims, No Drawings

HERBICIDE ANTIDOTE COMPOSITIONS AND METHOD OF USE

BACKGROUND OF THE INVENTION

In the past two to three decades, the crop yields obtained by American farmers and commercial agricultural companies have increased due to a number of factors, among them being scientific crop rotation, use of chemical fertilizers to stimulate crop plant growth, and also the use of various herbicidal compounds to kill unwanted weeds and grasses which compete with crop plants for soil nutrients. Examples of various herbicidal compounds which have been used in recent years include commercially available thiolcarbamate products such as Sutan ®, Ordram ®, Eptam ®, Knoxweed ®, Ro-Neet ®, Vernam ®, and the like. These herbicides are toxic to a large number of weeds when applied in varying concentrations for both pre-emergence and postemergent control. Particularly effective herbicides are the aforementioned Sutan ® and Vernam ® which are thiolcarbamates which have been found to be especially useful on controlling weeds in corn and soybeans, respectively. The thiolcarbamates, used alone or admixed with other herbicides, such as triazines, are used extensively at the present time.

A problem which as arisen in conjunction with the use of these compounds is that at herbicidally effective concentrations, the compounds have a tendency to injure and restrict the growth of the desired crop plant such as corn, soybeans, and the like.

Various attempts have been made to eliminate this problem by way of development of chemical compounds known as antidotes which are normally applied to the soil at the time of planting of the seeds and which are effective in protecting the crop plant from damage as a consequence of the application of a herbicide.

Examples of such herbicide antidote compositions which are commercially available include Eradicane ®, Sutan ®+, and Surpass ®+. These compositions and compounds are disclosed in U.S. Pat. Nos. 4,137,070 and 4,021,224. Other such antidote compounds are constantly being sought in order to provide a wider choice of available compounds which would be advantageous from an economic or efficacy standpoint, relative to the specific herbicide with which they are used, or the specific crop plant sought to be protected.

DESCRIPTION OF THE INVENTION

It has now been discovered that the semicarbazone compounds having the formula:

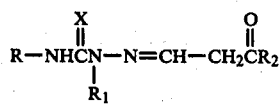

wherein R can be selected from the group consisting of alkyl groups having from about 1 to about 7 carbon atoms, aryl, and substituted aryl groups in which the substituent group can be lower alkyl having from about 1 to about 3 carbon atoms, substituted lower alkyls of from about 1 to about 3 carbon atoms in which the substituent group is halogen or nitro, lower alkoxy having from about 1 to about 3 carbon atoms; $R_1$ can be selected from the group consisting of hydrogen or lower alkyl having from about 1 to about 6 carbon atoms; $R_2$ can be selected from the group consisting of lower alkoxy having from about 1 to about 3 carbon atoms, and X is oxygen or sulfur, are effective as herbicide antidotes when used in conjunction with thiolcarbamate-type herbicides. It has been found that plants can be protected against injury by the thiolcarbamates alone or mixed with other compounds by adding to the soil an antidote compound as set forth above.

Preferred compounds which can be used in the compositions and method of the invention include:

1-(2-methoxycarbonylacetaldehyde)-2-methyl-4-phenyl-3-thiosemicarbazone, 1-(2-ethoxycarbonylacetaldehyde)-2-methyl-4-phenyl-3-semicarbazone, 1-(2-methoxycarbonylacetaldehyde)-2,4-dimethyl-3-thiosemicarbazone, 1-(ethylbenzoylacetate)-2-methyl-4-phenyl-3-thiosemicarbazone, 1-methylacetoacetate-2-methyl-4-phenyl-3-thiosemicarbazone, 1-(diethyloxalacetate)-2-methyl-4-phenyl-3-thiosemicarbazone, and 1-(2-ethylcarboxyethylidene)-2-methyl-4-phenylthiosemicarbazone.

The compounds of this invention utilized in the compositions and methods of the invention can be synthesized by reacting an appropriate amine with an alkyl-propiolate, in the presence of methyl alcohol solvent. After the reaction is complete, the solvent is separated from the desired end product under reduced pressure, leaving the liquid product.

The following examples illustrate methods of making the compounds of the present invention.

EXAMPLE I

Preparation of 1-(2-methoxycarbonylacetaldehyde)-2-methylphenyl-3-thiocarbazone

Nine grams (9.0 g) (0.05 mole) of 2-methyl-4-phenyl thiosemicarbazide, a compound having the formula

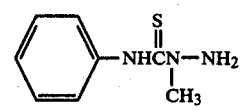

was suspended in 50 milliliters (ml) methyl alcohol. To that suspension was added, all at once, 4.45 ml (0.05 mole) of methyl propriolate. No change was observed in the temperature or color of the reaction mixture. The reaction mixture was then stirred at room temperature overnight. The reaction mixture became light yellow with white solids suspended therein. It was then heated with a heating mantle at 45°–50° C. for one hour. The white precipate dissolved and the solution turned a clear yellow. The solution was then stirred at ambient temperature for 2 hours. The solvent was Rinco stripped from the solution (bath temperature 25°–30° C.), yielding 13.15 g of 1-(2-methoxycarbonylacetaldehyde)-2-methyl-4-phenyl-3-thiosemicarbazone. The yield was 99.2% of theoretical, $n_D^{30} = 1.6185$.

EXAMPLE II

Preparation of 1-(2-methoxycarbonylacetaldehyde)-2-methylphenyl-3-thiocarbazone A solution was made by suspending 9 g (0.05 mole) of 2-methyl-4-phenyl thiosemicarbazone in 100 ml of methanol. To that suspension was added 4.45 ml methyl propiolate dissolved in 5 ml of methanol. The methyl propiolate was added to the suspension of 2-methyl-4-phenyl thiosemicarbazide all at once, with no change in temperature or color being observed. The reaction mixture was stirred at ambient temperature for 10 minutes and then heated with a heating mantle. The mixture became a clear yellow solution and this solution was refluxed for ½ hour, then stirred overnight at room temperature. The next day, the reaction mixture, now a yellow solution, was Rinco stripped, yielding 12.95 g of 1-(2-methoxycarbonylacetaldehyde)-2-methyl-4-phenyl-3-thiolsemicarbazone, $n_D^{30} = 1.6295$

EXAMPLE III

Preparation of 1-(2-ethylcarboxyethylidene)-2-methyl-4-phenylthiosemicarbazone A solution was made by suspending 9 g (0.05 mole) of 2-methyl-4-phenylthiosemicarbazone in 100 ml of methanol. To that suspension was added 4.9 g (0.05 mole) of ethylpropiolate dissolved in 10 ml of methyl alcohol. The ethylpropiolate was added to the suspension of 2-methyl-4-phenylthiosemicarbazone all at once, and no change was observed in the temperature or color of the reaction mixture.

The reaction mixture was then refluxed for two hours with a light green solution being formed. After two hours had elapsed, the mixture was cooled to room temperature and stirred at room temperature overnight. The following day, the reaction mixture, still a light green solution, was Rinco stripped, yielding 10.75 g of a heavy orange oil which was determined by chemical analysis to be the title compound.

The foregoing examples are illustrative of the general method of preparing the compounds of the instant invention. Other compounds falling within the scope of the invention can be prepared in an analogous manner starting with the appropriate starting materials as outlined above.

The compositions of this invention were tested in the following manner.

Testing

Stock solutions of the herbicide was prepared by diluting the requisite amount in water. Examples of solutions, compositions, and application rates are summarized in Table I.

TABLE I

| | Herbicide Stock Solutions | | | |
|---|---|---|---|---|
| | Composition | | Application | |
| Herbicide Name | Herbicide (mg)* | Water (ml) | ml/flat** | lb/acre |
| VERNAM ® 6E S—propyl-N,N—dipropyl thio- | 427 | 400 | 5 | 1.00 |
| | 2560 | 400 | 5 | 6.00 |

TABLE I-continued

| | Herbicide Stock Solutions | | | |
|---|---|---|---|---|
| | Composition | | Application | |
| Herbicide Name | Herbicide (mg)* | Water (ml) | ml/flat** | lb/acre |
| carbamate | | | | |

*The weight is measured in terms of mg of formulated herbicide. The formulations used contained about 72% active herbicide compound.
**The flats measure 5.95 inches by 9.5 inches. Approximately four (4) mg/flat is equal to one (1) lb/acre.

The herbicide was either incorporated into the soil prior to planting or applied to the soil after planting and prior to emergence of the plants. In some cases of pre-plant incorporation, the herbicide was incorporated into the soil along in preparaton for in-furrow application of the antidote; in others the herbicide solution was tank-mixed with the antidote solution prior to incorporation.

Stock solutions of each antidote compound were prepared at the desired concentrations by diluting the requisite amounts of each antidote in acetone. Examples of solution compositions, rates and application methods are summarized in Table II.

TABLE II

| Antidote Stock Solutions | | | | |
|---|---|---|---|---|
| Antidote: | | | | |
| Composition | | Application | | |
| Antidote (mg) | Acetone (ml) | ml/flat | lb/acre | Method |
| 95 | 15 | 0.30 | 1.00 | IF* |
| 95 | 15 | 1.50 | 5.00 | IF |

*IF = In-furrow surface application of antidote.

The antidote solutions were applied to the soil either by in-furrow surface application, or by pre-plant incorporation. In all cases of pre-plant incorporation, the antidote was tank-mixed with the herbicide prior to incorporation into the soil.

For in-furrow application, a one pint (473 cubic centimeter (cc)) sample of soil containing the previously incorporated herbicide was removed and retained from each planting flat. After leveling and furrowing the soil, seeds of the crop or weed species were planted ½ inch deep (1.27 centimeter). Each flat was divided in half by a wooden barrier. A stock solution of the antidote was atomized directly onto the exposed seeds and soil in the open furrow on one side of the barrier. The seeds in the entire flat were then covered with the previously removed soil. The antidotally untreated sections of flats were compared for observed differences which would indicate lateral movement of the antidote through the soil.

Control flats contained crops treated with herbicide only. All flats were placed on greenhouse benches where temperature was maintained between 70° and 90° F. (21.1° to 32.2° C.). The flats were watered by sprinkling as needed to assure good plant growth.

All of the soil used in the tests described herein was loamy sand soil treated with 50 parts per million (ppm) each of a commercially available fungicide, N-[(trichloromethyl)-thiol]-4-cyclohexene-1,2-dicarboximide, and 18-18-18 fertilizer, which contains 18% by weight equivalent each of nitrogen, phosphorus pentoxide, and potassium oxide.

Injury ratings were taken four weeks after application of the antidote. The effectiveness of the antidote was determined by visual comparison of crop injury which occurred in the test flats to that which occurred in the control flats.

The treated crops initially screened for herbicidal injury were milo, wheat, cotton, rice, barley, corn and soybeans. The compound was tested on the weed species watergrass (*Echinochloa crusgalli*).

KEY TO TABLE

Herbicide

VERNAM ®—S-propyl-N,N-di-propyl thiocarbamate

Application Methods

IF = In-furrow surface application of antidote (soil previously treated with herbicide only).
PPI = Pre-plant incorporation of herbicide or antidote. If both herbicide and antidote were preplant incorporated, a tank-mixed solution was used.
TM = Tank-mixed solution of herbicide and antidote.

All rates shown, for both herbicide and antidote, are in pounds per acre.

Injury Ratings

The injury to the crop or weeds (Table III) is shown as a percentage of damage done to the plants as compared to an evaluation of the overall undamaged state of the plants. The damage done to the plants is a function of the number of plants injured and the extent of injury to each plant. This rating is made four (4) weeks after application of the herbicide alone or of the herbicide in combination with the antidote.

effectiveness of the herbicide compound when used against watergrass, an undesirable weed.

The antidote compounds of the present invention can be used in any convenient form. Thus, the antidote compounds can be made into emulsifiable liquids, emulsifiable concentrates, liquids, wettable powder, powders, granules or other convenient forms. In its perferred form, the antidote compounds are admixed with the thiolcarbamates and incorporated into the soil prior to or after planting the seed. It is to be understood, however, that the thiolcarbamate herbicide can be incorporated into the soil and thereafter the antidote compound can be incorporated into the soil. Moreover, the seed can be treated with the antidote compound and planted into the soil which has been treated with herbicides or untreated with the herbicide and subsequently treated with the herbicide. The method of addition of the antidote compounds does not affect the herbicidal activity of the carbamate compounds.

The amount of antidote composition present can range between about 0.0001 to about 30 parts by weight per each part by weight of thiolcarbamate herbicide. The exact amount of antidote compound will usually be determined on economic ratios for the most effective amount usable.

When used in the claims of this application, the phrase "active herbicidal compound" is meant to include the active thiolcarbamates alone or the thiolcarbamates admixed with other active compounds such as the s-triazines. Also, the active herbicidal compound is

TABLE III

Antidotal Effectiveness
Herbicide - Vernam ® - S—propyl N,N—dipropyl thiolcarbamate

| Herbicide | | Antidote | | | Milo | Wheat | Cotton | Rice | Barley | Corn | Soybean | Water grass |
|---|---|---|---|---|---|---|---|---|---|---|---|---|
| Rate | Method | Name | Rate | Method | % Inj | % Inj | % Inj | % Inj | % Inj | % Inj | % Inj | % Inj |
| | PPI | X-1000* | 5.00 | IF | 95/95 | 90/90 | 65/65 | 90/90 | 90/90 | — | ** | —*** |
| | PPI | | 5.00 | IF | — | — | — | — | — | 90/90 | 25/35 | — |
| 3.00 | PPI | | 5.00 | PPI/TM | — | — | — | — | — | — | 10/40 | 100/100 |
| 3.00 | PPI | | 2.00 | PPI/TM | — | — | — | — | — | — | 20/40 | 100/100 |
| 1.25 | PPI | X-1001 | 5.00 | IF | 95/95 | 80/80 | 70/70 | 70/80 | 80/80 | — | — | — |
| 5.00 | PPI | | 5.00 | IF | — | — | — | — | — | 95/95 | 80/80 | — |
| 1.25 | PPI | X-1002 | 5.00 | IF | 99/95 | 85/85 | 30/30 | 90/90 | 97/97 | — | — | — |
| 5.00 | PPI | | 5.00 | IF | — | — | — | — | — | 99/99 | 30/60 | — |
| 4.00 | PPI | | 5.00 | PPI/TM | — | — | — | — | — | — | 35/60 | 100/100 |
| 4.00 | PPI | | 2.00 | PPI/TM | — | — | — | — | — | — | 45/60 | 100/100 |
| 4.00 | PPI | | 1.00 | PPI/TM | — | — | — | — | — | — | 60/60 | 100/100 |
| 1.25 | PPI | X-1003 | 5.00 | IF | 95/95 | 90/90 | 60/60 | 95/95 | 85/85 | — | — | — |
| 5.00 | PPI | | 5.00 | IF | — | — | — | — | — | 90/90 | 20/60 | — |
| 4.00 | PPI | | 1.00 | PPI/TM | — | — | — | — | — | — | 40/40 | 100/100 |
| 4.00 | PPI | | 2.00 | PPI/TM | — | — | — | — | — | — | 40/40 | 100/100 |
| 4.00 | PPI | | 5.00 | PPI/TM | — | — | — | — | — | — | 25/40 | 100/100 |
| 1.25 | PPI | X-1004 | 5.00 | IF | 95/95 | 90/90 | 60/60 | 95/95 | 60/85 | — | — | — |
| 5.00 | PPI | | 5.00 | IF | — | — | — | — | — | 90/90 | 50/60 | — |
| 4.00 | PPI | | 1.00 | PPI/TM | — | — | — | — | — | — | 30/40 | 100/100 |
| 4.00 | PPI | | 2.00 | PPI/TM | — | — | — | — | — | — | 30/40 | 100/100 |
| 4.00 | PPI | | 5.00 | PPI/TM | — | — | — | — | — | — | 30/40 | 100/100 |

*X-1000 - 1-(2-methoxycarbonylacetaldehyde)-2-methyl-4-phenyl3-thiosemicarbazone
X-1001 - 1-(ethylbenzoylacetate)-2-methyl-4-phenyl-3-thiosemicarbazone
X-1002 - 1-methylacetoacetate-2-methyl-4-phenyl-3-thiosemicarbazone
X-1003 - 1-(2-methoxycarbonylacetaldehyde-2,4-dimethyl-3-thiosemicarbazone
X-1004 - 1-(diethyloxalacetate)-2-methyl-4-phenyl-3-thiosemicarbazone
**In the results shown, the denominator represents that percentage of damage to the crop or weed caused by application of the herbicide by itself, while the numerator refers to that percentage of damage caused to the crop plant when both the herbicide and antidote were used with the crop plant in accordance with the specific methods described.
***A dash (—) indicates that no test was conducted at the specific herbicide or antidote levels or against the specific crop plants or weed type listed.

As seen from Table III above, the antidote compositions of this invention are particularly effective when used in conjunction with the thiolcarbamates and as applied toward soybean crop plants. They are less effective when used in conjunction with other crop plants such as rice and barley. As also seen above, in all instances the antidote composition did not reduce the different from the antidote compounds.

It is clear that the classes of herbicidal agents described and illustrated herein are characterized as effective herbicides exhibiting such activity. The degree of this herbicidal activity varies among specific compounds and among combinations of specific compounds within the classes. Similarly, the degree of activity to some extent varies among the species of plants to which a specific herbicidal compound or combination may be applied. Thus, selection of a specific herbicidal compound or combination to control undesirable plant species readily may be made. Within the present invention the prevention of injury to a desired crop species in the presence of a specific compound or combination may be achieved. The beneficial plant species which can be protected by this method is not intended to be limited by the specific crops employed in the examples.

The herbicidal compounds employed in the method of this invention are active herbicides of a general type. That is, the members of the classes are herbicidally effective against a wide range of plant species with no discrimination between desirable and undesirable species. The method of controlling vegetation comprises applying an herbicidally effective amount of the herein-described herbicidal compound to the area or plant locus where control is desired.

An "herbicide" as used herein means a compound which controls or modifies the growth of vegetation of plants. Such controlling or modifying effects include all deviations from natural development; for example, killing, retardation, defoliation, desiccation, regulation, stunting, tillering, stimulation, dwarfing and the like. By "plants" it is meant germinant seeds, emerging seedlings, and established vegetation, including the roots and above-ground portions.

The herbicides indicated in the tables are used at rates which produce effective control of undesirable vegetation. The rates are within the recommended amounts set forth by the supplier. Therefore, the weed control in each instance is commercially acceptable within the desired amount.

The antidotes are employed as a percentage or ratio of the herbicides, as hereinbefore stated.

As used herein, the term "antidote" refers to a chemical compound which when applied to the soil or crop seeds, either sequentially with or at the same time as a herbicide, has the effect of reducing the extent of damage caused to the crop plant by application of the herbicide, without substantial effect on the effectiveness of the herbicide against unwanted weeds and grasses. The term "antidotally effective amount" refers to that amount of the antidote compound which, when applied to the soil, or to the crop seed, is effective in substantially reducing or decreasing the amount of damage caused to the crop plant by the application of a herbicide when the herbicide is used in normal quantities known to those skilled in the art.

Also, the term "non-phytotoxic" refers to an amount of antidote which causes, at most, minor injury to the crop.

What is claimed is:

1. A herbicidal composition comprising an active thiolcarbamate herbicide compound and an antidotally effective amount of an antidote compound having the formula

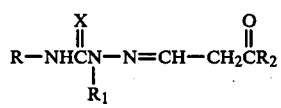

wherein R can be selected from the group consisting of alkyl groups having from about 1 to about 7 carbon atoms, aryl, and substituted aryl groups in which the substituent group can be lower alkyl having from about 1 to about 3 carbon atoms, substituted lower alkyls of from about 1 to about 3 carbon atoms in which the substituent group is halogen or nitro, lower alkoxy having from about 1 to about 3 carbon atoms; $R_1$ can be selected from the group consisting of hydrogen or lower alkyl having from about 1 to about 6 carbon atoms; $R_2$ can be selected from the group consisting of lower alkoxy having from about 1 to about 3 carbon atoms, and X is oxygen or sulfur; said compound being antidotally active with a thiolcarbamate herbicide compound and wherein said compound is present in an amount varying between about 0.0001 to 30 parts by weight for each part by weight of the active herbicidal compound.

2. A herbicidal composition as set forth in claim 1 wherein said active thiolcarbamate is selected from the group consisting of EPTC, S-ethyl N,N-diisobutylthiolcarbamate, S-propyl N,N-dipropylthiolcarbamate, S-2,3,3-trichloroallyl diisopropylthiolcarbamate, S-ethyl N-cyclohexyl N-ethyl thiolcarbamate or S-ethyl hexahydro-1H-azepine-1-carbothioate.

3. A herbicidal composition comprising an active S-alkyl thiolcarbamate pre-emergent herbicide and a soybean crop protective agent comprising an effective, but non-phytotoxic amount of 1-(2-methylcarbonylacetaldehyde)-2-methyl-4-phenyl-3-thiolsemicarbazone.

4. A herbicidal composition comprising an active S-alkyl thiolcarbamate pre-emergent herbicide and a soybean crop protective agent comprising an effective, but non-phytotoxic amount of 1-(2-ethylcarboxyethylidene)-2-methyl-4-phenyl-3-thiolsemicarbazone.

5. A herbicidal composition comprising an active thiolcarbamate herbicide compound and a non-phytotoxic antidotally effective amount of a 1-(2-carboalkoxyethyleneidene)-semicarbazone.

6. The herbicidal composition of claim 5 wherein said semicarbazone has the formula

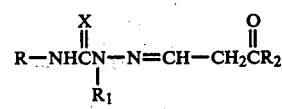

wherein R is alkyl or aryl, $R_1$ is hydrogen or lower alkyl, $R_2$ is alkoxy, and X is sulfur.

7. The method of controlling undesirable weeds in protecting crop plants comprising adding to the habitat thereof an herbicidally effective amount of a composition as set forth in claim 1.

8. The method of claim 7 wherein the crop is soybean and said composition is 1-(2-methoxycarbonylacetaldehyde)-2-methyl-4-phenyl-3-thiolsemicarbazone.

9. The method of claim 7 wherein the crop is barley and the antidote compound is 1-(2-methoxycarbonylacetaldehyde)-2-methyl-4-phenyl-3-thiolsemicarbazone.

10. The method of protecting a plant crop from injury due to an active herbicidal thiolcarbamate compound, comprising applying to the plant seed prior to planting a non-phytotoxic antidotally effective amount of a compound corresponding to the formula

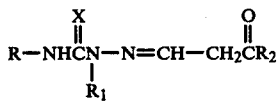

wherein R can be selected from the group consisting of alkyl groups having from about 1 to about 7 carbon atoms, aryl, and substituted aryl groups in which the substituent group can be lower alkyl having from about 1 to about 3 carbon atoms, substituted lower alkyls of from about 1 to about 3 carbon atoms in which the substituent group is halogen or nitro, lower alkoxy having from about 1 to about 3 carbon atoms; $R_1$ can be selected from the group consisting of hydrogen or lower alkyl having from about 1 to about 6 carbon atoms; $R_2$ can be selected from the group consisting of lower alkoxy having from about 1 to about 3 carbon atoms, and X is oxygen or sulfur.

11. The method according to claim 10 wherein the antidote compound is 1-(2-methoxycarbonylacetaldehyde)-2-methyl-4-phenyl-3-thiolsemicarbazone.

12. The method of protecting soybean from injury due to an active herbicidal thiolcarbamate control compound comprising applying to the soil a non-phytotoxic antidotally effective amount of a compound corresponding to the formula

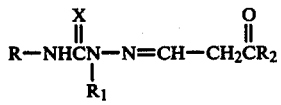

wherein R can be selected from the group consisting of alkyl groups having from about 1 to about 7 carbon atoms, aryl, and substituted aryl groups in which the substituent group can be lower alkyl having from about 1 to about 3 carbon atoms, substituted lower alkyls of from about 1 to about 3 carbon atoms in which the substituted group is halogen or nitro, lower alkoxy having from about 1 to about 3 carbon atoms; $R_1$ can be selected from the group consisting of hydrogen or lower alkyl having from about 1 to about 6 carbon atoms; $R_2$ can be selected from the group consisting of lower alkoxy having from about 1 to about 3 carbon atoms, and X is oxygen or sulfur; said compound being antidotally active with said thiolcarbamate herbicide.

13. The method according to claim 12 wherein R is alkyl or aryl, $R_1$ is hydrogen or lower alkyl, $R_2$ is alkoxy, and X is sulfur.

14. The method of controlling weeds and protecting a plant crop from injury due to an active thiolcarbamate herbicide compound, comprising applying to the soil a herbicidally effective amount of said herbicide and of a non-phytotoxic antidotally effective amount of a 1-(2-carboalkoxyethyleneidene)-semicarbazone, and semicarbazone being antidotally active with said thiolcarbamate herbicide.

15. The method of claim 14 wherein said semicarbazone has the formula

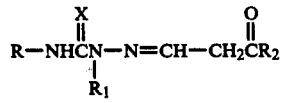

wherein R can be selected from the group consisting of alkyl groups having from about 1 to about 7 carbon atoms, aryl, and substituted aryl groups in which the substituent group can be lower alkyl having from about 1 to about 3 carbon atoms, substituted lower alkyls of from about 1 to about 3 carbon atoms in which the substituent group is halogen or nitro, lower alkoxy having from about 1 to about 3 carbon atoms; $R_1$ can be selected from the group consisting of hydrogen or lower alkyl having from about 1 to about 6 carbon atoms; $R_2$ can be selected from the group consisting of lower alkoxy having from about 1 to about 3 carbon atoms, and X is oxygen or sulfur.

16. The method of increasing the resistance of crop plant seed from injury from an active thiolcarbamate herbicide compound, comprising applying to the surface of said seed a coating of an antidotally effective, but substantially non-phytotoxic, amount of 1-(2-methoxycarbonylacetaldehyde)-2-methyl-4-phenyl-3-thiolsemcarbazone, said semicarbazone being antidotally active with said thiolcarbamate herbicide in the presence of said seed.

17. The method of protecting rice from injury due to an active herbicidal thiolcarbamate compound, comprising applying to the soil a non-phytotoxic antidotally effective amount of a compound having the formula

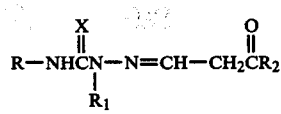

wherein R can be selected from the group consisting of alkyl groups having from about 1 to about 7 carbon atoms, aryl, and substituted aryl groups in which the substituent group can be lower alkyl having from about 1 to about 3 carbon atoms, substituted lower alkyls of from about 1 to about 3 carbon atoms in which the substituent group is halogen or nitro, lower alkoxy having from about 1 to about 3 carbon atoms; $R_1$ can be selected from the group consisting of hydrogen or lower alkyl having from about 1 to about 6 carbon atoms; $R_2$ can be selected from the group consisting of lower alkoxy having from about 1 to about 3 carbon atoms, and X is oxygen or sulfur.

18. The method for protecting soybean from injury due to an active S-alkyl thiolcarbamate pre-emergent herbicide comprising applying to the soil in the vicinity of the soybean seed an effective but non-phytotoxic amount of 1-(2-methoxycarbonylacetaldehyde)-2-methyl-4-phenyl-3-thiolsemicarbazone.

19. As a new composition of matter, compounds of the formula

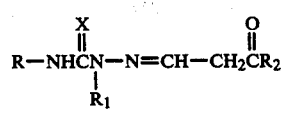

wherein R can be selected from the group consisting of alkyl groups having from about 1 to about 7 carbon atoms, aryl, and substituted aryl groups in which the substituent group can be lower alkyl having from about 1 to about 3 carbon atoms, substituted lower alkyls of from about 1 to about 3 carbon atoms in which the substituent group is halogen or nitro, lower alkoxy having from about 1 to 3 carbon atoms; $R_1$ can be selected from the group consisting of hydrogen or lower alkyl having from about 1 to about 6 carbon atoms; $R_2$ can be selected from the group consisting of lower alkoxy having from about 1 to about 3 carbon atoms, and X is oxygen or sulfur.

* * * * *